United States Patent [19]
Sanders

[11] Patent Number: 5,897,579
[45] Date of Patent: Apr. 27, 1999

[54] METHOD OF RELIEVING AIRWAY OBSTRUCTION IN PATIENTS WITH BILATERAL VOCAL IMPAIRMENT

[75] Inventor: Ira Sanders, New York, N.Y.

[73] Assignee: Mount Sinai School of Medicine, New York, N.Y.

[21] Appl. No.: 08/979,207

[22] Filed: Nov. 26, 1997

Related U.S. Application Data

[63] Continuation of application No. 08/823,861, Mar. 25, 1997, abandoned, which is a continuation of application No. 08/306,632, Sep. 15, 1994, abandoned.

[51] Int. Cl.$^6$ .................................................. A61N 1/36
[52] U.S. Cl. ................................................................. 607/42
[58] Field of Search ............................... 607/42, 48, 134

[56] References Cited

U.S. PATENT DOCUMENTS

| | | | |
|---|---|---|---|
| 3,796,221 | 3/1974 | Hagfors | 607/42 |
| 5,016,647 | 5/1991 | Sanders | 607/134 |
| 5,111,814 | 5/1992 | Goldfarb | 607/42 |

FOREIGN PATENT DOCUMENTS

| | | | |
|---|---|---|---|
| 2493154 | 5/1982 | France | 607/42 |
| 9219318 | 11/1992 | WIPO | 607/42 |

OTHER PUBLICATIONS

Intrel II Physician Instruction Manual, "Using Medtronic Model 3886 Lead, Model 7495 Extension and Model 7424 Itrel Implantable Pulse Generator" (published by Medtronic regarding Sacral nerve stimulation) 1993.
Peckham, 1991 IEEE Trans. Biomed. Eng. 28:530.
Sanders, 1991, Otolaryngologic Clinics of North America 24:1253–1274.
Jacobs et al., 1990, Ann. Otol. Rhinol. Laryngol. 99:167.
Sanders et al., 1989, Ann. Otol. Rhino. Laryngol 98:339–345.
Broniatowski et al., 1986, Otolaryngol. Head Neck Surg. 94:41.
Zrunek et al., "Functional electrical stimulation in bilateral recurrent nerve palsy in sheep: Functional and Biochemical results", *Proceedings of the 2nd Vienna International Workshop on Functional Electrostimulation*, Sep. 14–21, 1986, Vienna Austria.
Broniatowski et al., 1985, Laryngoscope 95:1194.
Sanders and Biller, "Considerations in Development of a Laryngeal Pacemaker: A Feasibility Study" presented Sep. 1985, Research Forum of the American Academy of Otolaryngology, Atlanta
Obert et al., 1984, Arch. Otolaryngol. 110:88.
Zrunek et al. Abstract Laryngol. Rhinol. Otol. 655: pp. 621–7 (Nov. 1986 West Germany).
Zrunek et. al Abstract laryngol. Rhinol. Otol. 65: pp. 292–6 (May 1986 West Germany).

(List continued on next page.)

*Primary Examiner*—William E. Kamm
*Attorney, Agent, or Firm*—Baker & Botts, LLP

[57] ABSTRACT

Airway obstruction in a patient with bilateral impairment of mobility of the vocal cords may be relieved by a method comprising implanting an electrode of a neural electrical stimulator comprising a pulse generator such that the electrode stimulates the posterior cricoarytenoid muscle, thereby resulting in abduction of the vocal cords and relief of airway obstruction. This method of relieving airway obstruction is based, at least in part, on the discovery that the implantation of an electrical pulse generator previously used in the stimulation of the spinal cord into a dog model of human BVCP was successful in chronically stimulating the PCA without the development of significant muscle abnormality. In various embodiments, electrical stimulation of the PCA may be accomplished either by the manual or magnetic activation of a switch which triggers the firing of the pulse generator or, alternatively, the power source of the pulse generator may be adapted to provide an electrical stimulus automatically in a predetermined sequence such that vocal cord abduction and adduction are caused to occur in a sequence selected to correspond to the respiratory needs of the patient.

7 Claims, 2 Drawing Sheets

OTHER PUBLICATIONS

Otto Templer, "Coordinated pacing of vocal cord abductors in recurrent laryngeall nerve paralysis" presented Sep. 1984, Research Forum of the American Academy of Otolaryngology, Las Vegas, NV.

Rice and Burstein, 1983, Arch. Otolaryngol. Head Neck Surg. 109:480.

Tucker, 1983, Larynogoscope 93:295.

Zrunek et al., "Direct electrical stimulation of th posterior cricoarytenoid muscle" *Proceedings of the 1st Vienna International Workshop on Functional Electrostimulation*, Oct. 19–22, 1983, Vienna, Austria.

Hambrecht, 1979, Ann. Oto, Rhinol. Laryngol. 88:729.

Kirchner, 1979, Laryngoscope 89:1179.

Erlandson, 1978, Scand, J. Urol. Nephrol 44 (Suppl.) :31.

Zealer and Dedo, 1977, Acta Otolaryngol. 83:514.

Glenn, 1976, Ann. Surg. 183:566.

Holinger et al., 1976, Ann. Otol. Rhinol. Laryngol. 85:428.

Hengerer, 1973, Arch. Otolaryngol. Head Neck Surg. 97:247.

Doyle et al., 1967, Laryngoscope 77:1245.

Siribodhi et al., 1963, Laryngoscope 73:148.

Woodman, 1946, Arch. Otolaryngol. Head Neck Surg. 43:63.

METHOD OF RELIEVING AIRWAY OBSTRUCTION IN PATIENTS WITH BILATERAL VOCAL IMPAIRMENT

This application is a continuation of application Ser. No. 08/823,861, filed on Mar. 25, 1997, now abandoned, which is a continuation of application Ser. No. 08/306,632, filed on Sep. 15, 1994, now abandoned.

1. INTRODUCTION

The present invention relates to a method of relieving airway obstruction in a patient with bilateral impairment of mobility of the vocal cords, comprising implanting an electrode of a neural electrical stimulator such that the electrode stimulates the posterior cricoarytenoid muscle, thereby resulting in abduction of the vocal cords and relief of airway obstruction.

2. BACKGROUND OF THE INVENTION

2.1. BILATERAL VOCAL CORD PARALYSIS

Bilateral vocal cord paralysis ("BVCP") is a condition in which both recurrent laryngeal nerves ("RLN") are severed and all the intrinsic laryngeal muscles, except for the cricothyroid, are paralyzed (Holinger et al., 1976, Ann. Otol. Rhinol. Laryngol. 85: 428). The vocal cords assume a position near the midline which allows for an acceptable voice. Because of the loss of function of the posterior cricoarytenoid muscle ("PCA"), however, the vocal cords no longer abduct during inspiration. If left untreated, the individual ultimately suffocates. The standard initial therapy for this condition is to bypass the obstruction by performing a tracheostomy. Although crudely efficient in restoring an airway, tracheostomy requires a great deal of care and involves a number of serious social disadvantages and social complications (Myers and Stool, 1985, in *Tracheotomy*, Myers et al., eds, New York, Churchill Livingston).

Numerous surgical procedures have been proposed to rehabilitate the patient with BVCP and allow for removal of the tracheostomy tube. Currently, the most common clinical procedures include vocal cord lateralization (Kirchner, 1979, Laryngoscope 89: 1179), and arytenoidectomy (Woodman, 1946, Arch. Otolaryngol. Head Neck Surg. 43: 63), which widen the glottic opening by permanently altering the vocal cord. The disadvantage to these procedures is that the widened glottis increases the patient's susceptibility to aspiration while simultaneously decreasing the quality of the voice.

Another means of rehabilitation involves reanastomosis of the RLN. However, the RLN contains both abductor and adductor fibers and upon its reanastomosis, these fibers regenerate in an indiscriminate manner, so that the resulting laryngeal movement is uncoordinated and synkinetic (Doyle et al., 1967, Laryngoscope 77: 1245; Siribodhi et al., 1963, Laryngoscope 73: 148).

An entirely different approach to rehabilitation attempts to restore the function of the PCA muscle by reinnervation with nerves presumed to carry neural activity synchronous with inspiration. These nerves are either connected to the severed distal stump of the RLN or the RLN nerve branch which enervates the PCA, or are implanted directly into the PCA. Nerves used in these procedures include the phrenic, cervical nerve trunk, ansa cervicalis, and nerves to the cricothyroid, sternohyoid, and omohyoid muscles (Jacobs et al., 1990, Ann. Otol. Rhinol. Laryngol. 99: 167; Rice and Burstein, 1983, Arch. Otolaryngol. Head Neck Surg. 109: 480; Hengerer, 1973, Arch. Otolaryngol. Head Neck Surg. 97: 247; Tucker, 1983, Laryngoscope 93: 295).

It has been theorized that restoring denervated PCA function may be accomplished with a functional electrical stimulation system (Sanders, 1991, Otolaryngologic Clinics of North America 24: 1253–1274, citing Broniatowski et al., 1986, Otolaryngol. Head Neck Surg. 94: 41; Broniatowski et al., 1985, Laryngoscope 95: 1194; Hollinger et al., 1976, Ann. Otol. Rhinol. Laryngol. 85: 4285; Obert et al., 1984, Arch. Otolaryngol. 110: 88; Otto and Templer, "Coordinated pacing of vocal cord abductors in recurrent laryngeal nerve paralysis", presented at the Research Forum of the American Academy of Otolaryngology, Las Vegas, September, 1984; Sanders and Biller, "Considerations in the development of a laryngeal pacer", presented at the Research Forum of the American Academy of Otolaryngology, Atlanta, September, 1985; Zealar and Dedo, 1977, Acta Otolaryngol. 83: 514; Zrunek et al., "Direct electrical stimulation of the posterior cricoarytenoid muscle" in Proceedings of the 1st Vienna International Workshop on Functional Electrostimulation, Vienna, Austria, Oct. 19–22, 1983; Zrunek et al., "Functional electrical stimulation in bilateral recurrent nerve palsy in sheep: Functional and biochemical results" in Proceedings of the 2nd Vienna International Workshop on Functional Electrostimulation", Vienna, Austria, Sep. 14–21, 1986).

Of all the possible tissues that could be stimulated by such a system, denervated muscle is the least studied (Sanders, 1991, Otolaryngologic Clinics of North America 24: 1253–1274), and has been associated with a variety of technical problems.

Sanders et al., 1989, Ann. Otol. Rhinol. Laryngol. 98: 339–345 reports successful transmucosal electrical stimulation of laryngeal muscles in dogs, and states that transmucosal stimulation appears promising as a diagnostic technique for correlating particular vocal cord movements and thresholds of activation with specific laryngeal disorders. However, this technique cannot be used therapeutically because the stimulation of mucosa causes pain in the awake patient.

Studies of stimulation of denervated PCA in dogs suggest that in order to achieve a sufficient firing frequency, an overly large power supply would be required (Sanders, 1991, Otolaryngologic Clinics of North America 24: 1253–1274, see pp. 1257–1262). It has been suggested that this problem might be solved by limiting the duration or frequency of firing, or by augmenting artificial stimulation with physiologic stimulation recruited from intact nerves.

Another problem to be addressed is the undesirable spread of current to stimulate muscles other than the PCA (Id., pp. 1262–1263). In BVCP, the intrinsic muscles of the larynx are paralyzed and sensation is lost in the subglottic larynx and trachea, so that high current flows required to stimulate the denervated PCA can easily spread to excite these structures. It has been suggested that the current might be further localized by manipulating such factors as the size, location, and orientation of the electrodes, variables which constitute what has been referred to as the "electrode array". A pilot study of chronic stimulation of denervated PCA in dogs indicated that chronically stimulated muscle resisted atrophy and was more responsive to electrical stimulation than muscle that was not chronically stimulated (Id., pp. 1270–1272).

2.2. FUNCTIONAL ELECTRICAL STIMULATION

Functional electrical stimulation ("FES") is the application of stimulation devices to nerves to rehabilitate neurological deficits. The most successful FES system to date is the cardiac pacer which has become a routine part of cardiac disease therapy (Lynch, 1982, "Cardiovascular Implants" in

*Implants*, Lynch, ed., New York, Van Nostrand Rheinhold). There are a variety of other FES systems, however. The most heavily researched are FES systems to restore locomotion to paraplegics and arm motion to quadriplegics (Peckham, 1991, IEEE Trans. Biomed. Eng. 28: 530). Other motor control devices restore bladder control to paraplegics and diaphragm function to high quadriplegics (Erlandson, 1978, Scand. J. Urol. Nephrol. 44(Suppl.): 31; Glenn, 1976, Ann. Surg. 183: 566). There are also FES devices designed to rehabilitate sensory deficits, such as the cochlear implant (Hambrecht, 1979, Ann. Otol. Rhinol. Laryngol. 88: 729).

Neural FES devices which may be used to stimulate spinal cord, phrenic nerve, cochlea, paralyzed limbs or sacral nerve are available. Sacral nerve FES systems are currently being investigated for use in the management of pelvic dysfunctions which have proved refractory to appropriate conventional treatments. Such dysfunctions include urinary incontinence due to detrusor instability or sphincter instability, voiding difficulties such as dysfunctional flow and urinary retention, urgency/frequency syndromes associated with urethral syndrome and prostatism, recurrent urinary tract infections and pelvic pain.

3. SUMMARY OF THE INVENTION

The present invention relates to a method of relieving airway obstruction in a patient with bilateral impairment of mobility of the vocal cords, comprising implanting an electrode of a neural electrical stimulator comprising a pulse generator such that the electrode stimulates the posterior cricoarytenoid muscle ("PCA"), thereby resulting in abduction of the vocal cords and relief of airway obstruction.

The present invention is based, at least in part, on the discovery that the implantation of an electrical pulse generator previously used in the stimulation of the spinal cord into a dog model of human BVCP was successful in chronically stimulating the PCA without the development of significant muscle abnormality.

In various embodiments of the invention, electrical stimulation of the PCA may be accomplished either by the manual or magnetic activation of a switch which triggers the firing of the pulse generator or, alternatively, the power source of the pulse generator may be adapted to provide an electrical stimulus automatically in a predetermined sequence such that vocal cord abduction and adduction are caused to occur in a sequence selected to correspond to the respiratory needs of the patient.

4. BRIEF DESCRIPTION OF THE DRAWINGS

A nonlimiting embodiment of the invention is illustrated in the appended drawings in which FIG. 1A is a side view of a patient having a surgically implanted embodiment of the invention, comprising a switch, a power source and an electrode of a neural electrical stimulator.

5. DETAILED DESCRIPTION OF THE INVENTION

Figure 1A:
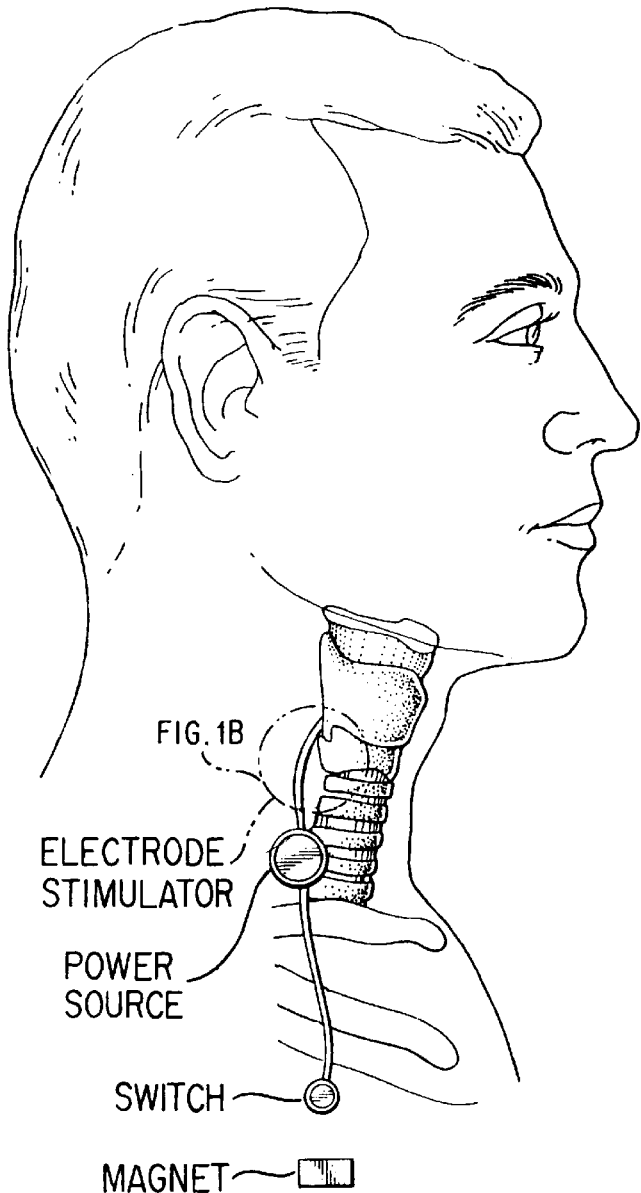
FIG. 1B shows the electrode of a neural electrical stimulator in contact with the posterior cricoarytenoid muscle.
Figure 1B:
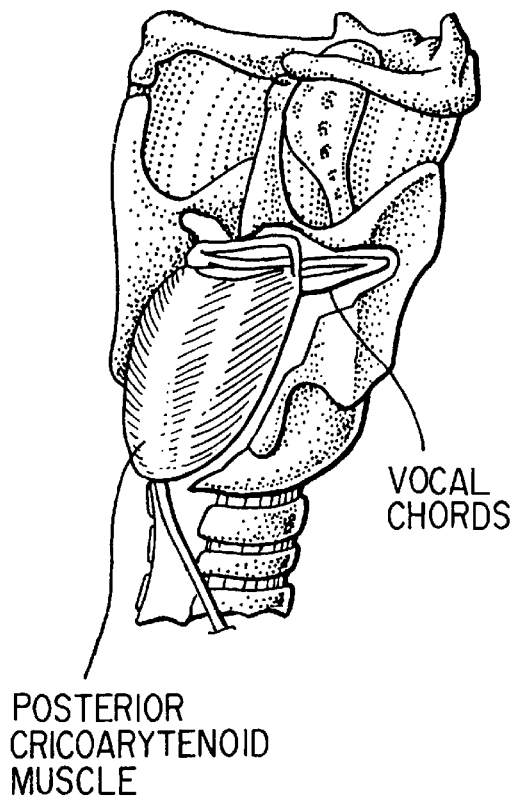
Figure 2A:
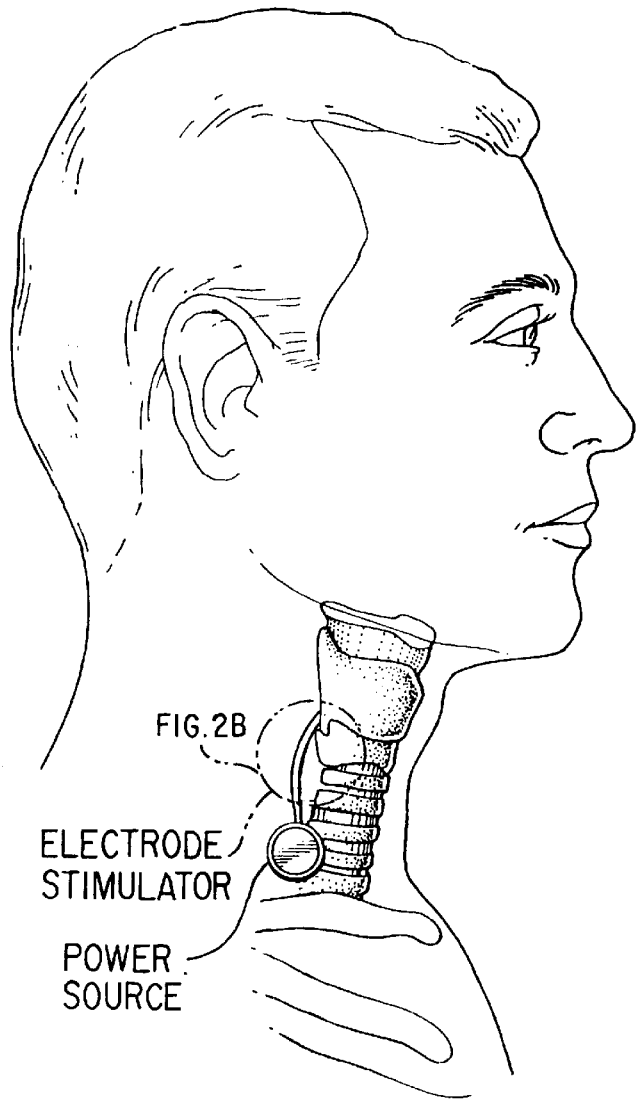
FIG. 2A is a side view of a patent having a surgically implanted embodiment of the invention, comprising a power source that provides a series of electrical stimuli via an electrode of a neural electrical stimulator.
Figure 2B:
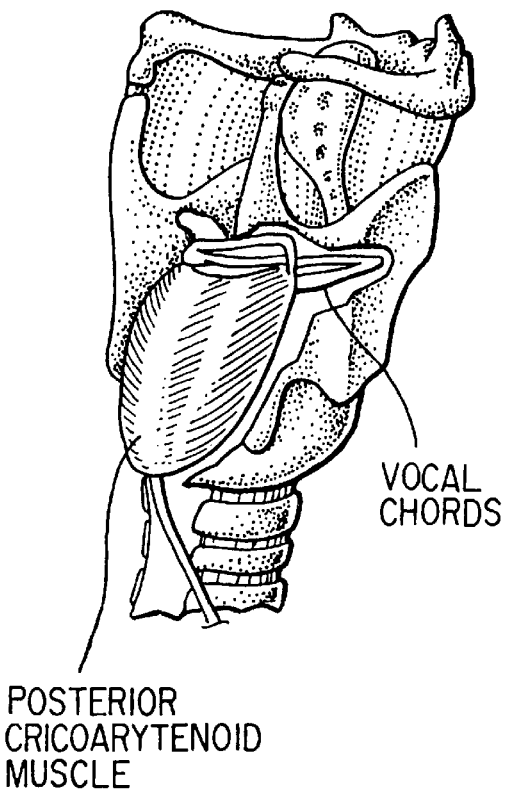
FIG. 2B shows the electrode of a neural electrical stimulator in contact with the posterior cricoarytenoid muscle.

The present invention provides for a method of relieving airway obstruction in a patient with bilateral impairment of mobility of the vocal cords, comprising implanting an electrode of a neural electrical stimulator comprising a pulse generator such that the electrode stimulates the posterior cricoarytenoid muscle ("PCA"), thereby resulting in abduction of the vocal cords and relief of airway obstruction.

The phrase "bilateral impairment of mobility of the vocal cords" refers to a decreased ability of the vocal cords to abduct, such decrease being sufficient to result in respiratory compromise of the patient, which is manifested by the subjective symptom of shortness of breath and/or the objective clinical signs of stridor and restricted peak inspiratory flow. The impairment of mobility may result from a deficit in nerve or muscle or both, but the PCA muscle must be capable of being electrically stimulated to cause abduction of the vocal cords (see below). For example, but not by way of limitation, the impairment may result from impairment of an upper motor neuron, a lower motor neuron, the recurrent laryngeal nerve, or a mechanical lesion such as vocal cord scarring, cricoarytenoid arthritis or an infiltrative lesion.

The term "abduction of vocal cords" refers to that amount of abduction sufficient to permit inspiration, to relieve stridor, and/or to increase the peak inspiratory flow.

The term "relief of airway obstruction" refers to a subjective or objective improvement in the clinical symptoms and/or signs of the patient resulting from the bilateral impairment of mobility of the vocal cords. In a preferred, nonlimiting embodiment of the invention, this may be measured by an increase in the peak inspiratory flow to a level above between 1 and 1.5 liters/sec.

The term neural electrical stimulator refers to a device such as a device used for stimulation of the spinal cord or peripheral nerves. For example, but not by way of limitation, such devices include the Itrel II System for spinal cord stimulation, as sold by Medtronic, Inc., which comprises the Model 7424 Implantable Pulse Generator, the Model 3886 Lead (although a 3487A PISCES-Quad Lead may also be used), and the Model 7495 Extension, or similar devices (and see the Itrel II Physician Instruction Manual published by Medtronic, regarding the system for sacral nerve stimulation), as well as other devices designed expressly for muscle stimulation but comprising substantially the features of the above-mentioned neural stimulator devices.

In one series of embodiments, the present invention relates to a method of relieving airway obstruction in a patient with bilateral impairment of the vocal cords, said method comprising the steps of (1) surgically implanting at least one electrode of a neural electrical stimulator such that the electrode is capable of stimulating the PCA to cause abduction of the vocal cords, said stimulator being electrically connected to an electric power source adapted to provide an electrical stimulus in response to the activation of a switch, and (2) manually activating the switch each time electrical stimulation and abduction of the vocal cords is required, thereby causing abduction and relief of airway obstruction. Electrical stimulation and abduction of the vocal cords is considered to be required when the patient is subjectively or objectively in need of increased respiration.

Such a method may comprise activation, by the patient, during times of aerobic stress such as during exercise, emotional excitement, exposure to high altitude, etc. The patient may activate the device and then entrain his inspirations to correspond to stimulation times.

In a related embodiment, the switch may be activated (and/or deactivated) magnetically by means of an external magnet. For example, and not by way of limitation, a magnet may be placed at a position over the location of the device, such that the magnet is brought into a position which activates (or deactivates) the device.

In another example, and not by way of limitation, the device may be activated by a reed switch located under the skin of the patient, so that the patient may press his skin at a position over the reed switch so as to activate (or deactivate) the device.

In an alternate series of embodiments, the present invention provides for a method of relieving airway obstruction in a patient with bilateral impairment of mobility of the vocal cords, said method including the steps of (1) surgically implanting at least one electrode of a neural electrical stimulator such that the electrode is capable of stimulating the PCA to cause abduction of the vocal cords, said stimulator being electrically connected to an electric power source adapted to provide an electrical stimulus automatically in a predetermined sequence such that vocal cord abduction and adduction are caused in sequence, said predetermined sequence being selected so as to correspond to the respiratory needs of the patient.

The phrase "respiratory needs of the patient" refers to the amount of ventilation necessary and/or desirable to satisfy the patient's oxygen requirements and/or render the patient subjectively comfortable during periods of aerobic stress, such as periods of exertion, emotional excitement, exposure to high altitude, etc.

The term "predetermined sequence" refers to a schedule of stimulation and rest cycles to mimic natural inspiration and expiration. For example, and not by way of limitation, the predetermined sequence may be 1.5 seconds of inspiration followed by 3.5 seconds of rest.

In certain, nonlimiting embodiments, the electrical stimulator includes a switch for activating and deactivating the stimulator. In an additional nonlimiting embodiment, the method includes a step of activating the stimulator by means of said switch during a time of aerobic stress, and deactivating the stimulator by means of said switch when the aerobic stress has ceased.

The foregoing methods of stimulating the PCA may be observed to result in an increase in the tone of the PCA, with the consequence that the vocal cord comes to rest in a more lateral position between stimulations (resulting in decreased obstruction). The phrase "more lateral" refers to the resting position of the vocal cord in relation to the midline.

For example, and not by way of limitation, a specific embodiment of the invention may be practiced as follows (and see the Itrel II Physician Instruction Manual published by Medtronic, regarding the system for sacral nerve stimulation). The lower edge of the cricoid and PCA muscles may be exposed by surgical dissection. Then, using a trochar, a tunnel may be made between the PCA muscle and the cricoid cartilage. An electrode of a neural stimulator, such as the Itrel II System described above (e.g. a linear electrode array), may then be passed through the trochar. The trochar may be removed, and the electrode fixed in position by suturing a plastic anchor to the inferior border of the cricoid cartilage. During such a procedure, it is desirable (1) not to surgically expose the muscle, as this may cause scarring; (2) to place the electrode between the muscle and the cartilage; and (3) to anchor the electrode at the location where it exits the muscle.

The foregoing embodiments may also incorporate the following features. In a specific, nonlimiting embodiment of any of the foregoing methods, a matrix of electrodes may be implanted into the PCA such that the geometry of the electrode configuration may be changed after implant in order to optimize the degree of abduction associated with a particular stimulus intensity, given the variability in electrode placement which may be associated with certain implantation techniques, such as blind trocar placement. In a related embodiment, such an array of electrodes permits alteration in the geometry of the electrode configuration subsequent to changes in the geometry of the PCA which may, for example, occur as a result of the reversal of disuse atrophy which may be caused by chronic electrical stimulation.

The present invention is supported by data from experiments in which three dogs underwent recurrent laryngeal nerve section and implantation of an Itrel neural stimulator using an inferior surgical approach, as described above. The PCA muscles were then continuously stimulated for three months using a 1.5 seconds on, 8 seconds off schedule. Vocal cord abduction was observed to range from 1–2 mm in all dogs during this period. After the three month period, the dogs were sacrificed and the PCA muscles excised. Histology of the PCAs showed retention of normal appearing muscle fibers, indicating that chronic stimulation was not associated with significant muscle histopathology.

Various publications are cited herein, which are hereby incorporated by reference in their entireties.

What is claimed is:

1. A method of relieving airway obstruction in a human patient with bilateral vocal cord impairment, wherein the patient has a denervated posterior cricoarytenoid muscle, said method including the steps of (1) surgically implanting into the posterior cricoarytenoid muscle of the patient at least one electrode of a neural electrical stimulator connected to an electrical power source and having a switch, such that when the switch is activated the power source provides an electrical stimulus via the electrode thereby stimulating the posterior cricoarytenoid muscle and causing abduction of the vocal cords; and (2) manually activating the switch each time relief of airway obstruction is required.

2. A method according to claim 1, wherein the step of manually activating the switch comprises activating a magnetically-actuable switch by placing an external magnet at a position over the location of the magnetically-actuable switch.

3. A method according to claim 1, wherein the step of manually activating the switch each time relief of airway obstruction is required comprises manually activating a reed switch by changing the reed switch from a position of deactivation to a position of activation each time relief of airway obstruction is required.

4. A method according to claim 1, further comprising surgically implanting at least one additional electrode of the electrical stimulator into the patient under the posterior cricoarytenoid muscle prior to manually activating the switch.

5. A method according to claim 1, further comprising the step of manually activating the switch causing the vocal cords to rest in a more lateral position between stimulations relative to a non-stimulated and immobile vocal cord.

6. A method of relieving airway obstruction in a human patient with bilateral vocal cord impairment, wherein the patient has a denervated posterior cricoarytenoid muscle, said method including the steps of (1) surgically implanting into the posterior cricoarytenoid muscle of the patient at least one electrode of a neural electrical stimulator such that when the electrode provides an electrical stimulus, the posterior cricoarytenoid muscle is stimulated, thereby causing abduction of the vocal cords;

(2) connecting said stimulator to an electrical power source which provides a series of electrical stimuli via the electrode when the stimulator is activated;

(3) selecting a series of electrical stimuli so as to correspond to the respiratory needs of the patient such that vocal cord abduction and adduction are caused in a predetermined sequence which effectively relieves airway obstruction in the patient;

(4) activating the stimulator. wherein activating the stimulator results in providing the series of electrical stimuli via the electrode in the predetermined sequence.

7. A method according to claim 6, wherein step (4) further comprises activating the stimulator by changing a switch from a position of deactivation to a position of activation.

* * * * *